United States Patent [19]
Porro et al.

[11] Patent Number: 5,834,430
[45] Date of Patent: Nov. 10, 1998

[54] POTENTIATION OF ANTIBIOTICS

[75] Inventors: Massimo Porro, Siena, Italy; Martti Varra, Haartmaninkatu, Finland

[73] Assignee: BiosYnth S.r.l., Italy

[21] Appl. No.: 456,112

[22] Filed: May 31, 1995

[51] Int. Cl.$^6$ .......................... A61K 38/00; A61K 38/12; A61K 38/04; C07K 5/00

[52] U.S. Cl. ............................... 514/14; 514/15; 514/16; 514/17; 514/11; 530/319; 530/327; 530/328; 530/329; 530/317

[58] Field of Search .................................. 514/14, 15, 11, 514/16, 17; 530/319, 327, 328, 329, 317

[56] References Cited

U.S. PATENT DOCUMENTS

| | | | |
|---|---|---|---|
| 5,225,399 | 7/1993 | Zasloff et al. | 514/13 |
| 5,358,933 | 10/1994 | Porro | 514/15 |
| 5,371,186 | 12/1994 | Porro | 530/328 |
| 5,470,950 | 11/1995 | Maloy et al. | 530/324 |
| 5,654,274 | 8/1997 | Kari | 514/12 |

FOREIGN PATENT DOCUMENTS 9012587  11/1990  WIPO.

OTHER PUBLICATIONS

Science, "Molecular Mapping and Detoxification of the Lipid A Binding Site by Synthetic Peptides", Alessandro Rustici et al., vol. 259, 15 Jan. 1993, 361–365.

*Primary Examiner*—Cecilia J. Tsang
*Assistant Examiner*—Jennifer Harle
*Attorney, Agent, or Firm*—Hedman, Gibson & Costigan, P.C.

[57] ABSTRACT

The present invention is concerned with methods of potentiating an antibiotic. The invention also includes compositions of an antibiotic and a peptide having units of the formula:

(a) $(A)_n$ wherein A is Lysine or Arginine and n is an integer with a minimum value of 7.

(b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a minimum value of 3; and (c) $(ABC)_p$ wherein A is a cationic amino acid which is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2. The compositions have potentiated antibiotic activity.

45 Claims, 5 Drawing Sheets

/ 5,834,430 /

POTENTIATION OF ANTIBIOTICS

FIELD OF THE INVENTION

The present invention is concerned with providing a method of potentiating antibiotics and new compositions which comprise an antibiotic and a potentiating agent which comprises a peptide which binds to lipopolysaccharide (LPS).

BACKGROUND OF THE INVENTION

Antibiotics are widely used in medicine for the treatment of infections caused by susceptible microbiological organisms. Many of these drugs have toxic side effects and/or require increased doses for the treatment of certain infections. The applicants have discovered that many different types of antibiotics, which are chemically dissimilar, may be potentiated if an effective amount of a peptide which binds to LPS is coadministered with an antibiotic to treat an infection which is caused by a susceptible organism. Certain of these peptides are disclosed in U.S. Pat. No. 5,371,186, which is incorporated by reference.

SUMMARY OF THE INVENTION

The applicant has discovered that antibiotics are potentiated when they are coadministered with peptides which contain the basic amino acid units (homopolymer units) as well as the basic and hydrophobic amino acids (heteropolymer units) according to the formulae: $(A)_n$, $(AB)_n$, and $(ABC)_n$ where A is any cationic amino acid (at a pH of about 7.0); B and C are any hydrophobic amino acid, both (the aliphatic cationic amino acid and the hydrophobic amino acid) that are characterized by solvent parameter values equal to or greater than +1.5kcal/mol and −1.5 kcal/mol respectively, may be coadministered with an antibiotic to potentiate the antibiotic effect of the antibiotic. The potentiation of the antimicrobial effect of an antibiotic allows the dose of the antibiotic to be reduced while achieving the same in vivo or in vitro effect.

Accordingly, it is a primary object of the invention to provide a means of potentiating an antibiotic.

It is also an object of the invention to provide novel compositions for the treatment or prophylaxis of microbial infections.

It is also an object of the invention to provide novel methods for the treatment or prophylaxis of microbial infections which use reduced doses of antibiotic drugs.

It is also an object of this invention to provide novel compositions and methods for the treatment of microbial infections.

These and other objects of the invention will become apparent from the appended specification.

DETAILED DESCRIPTION OF THE INVENTION

Figure 1:
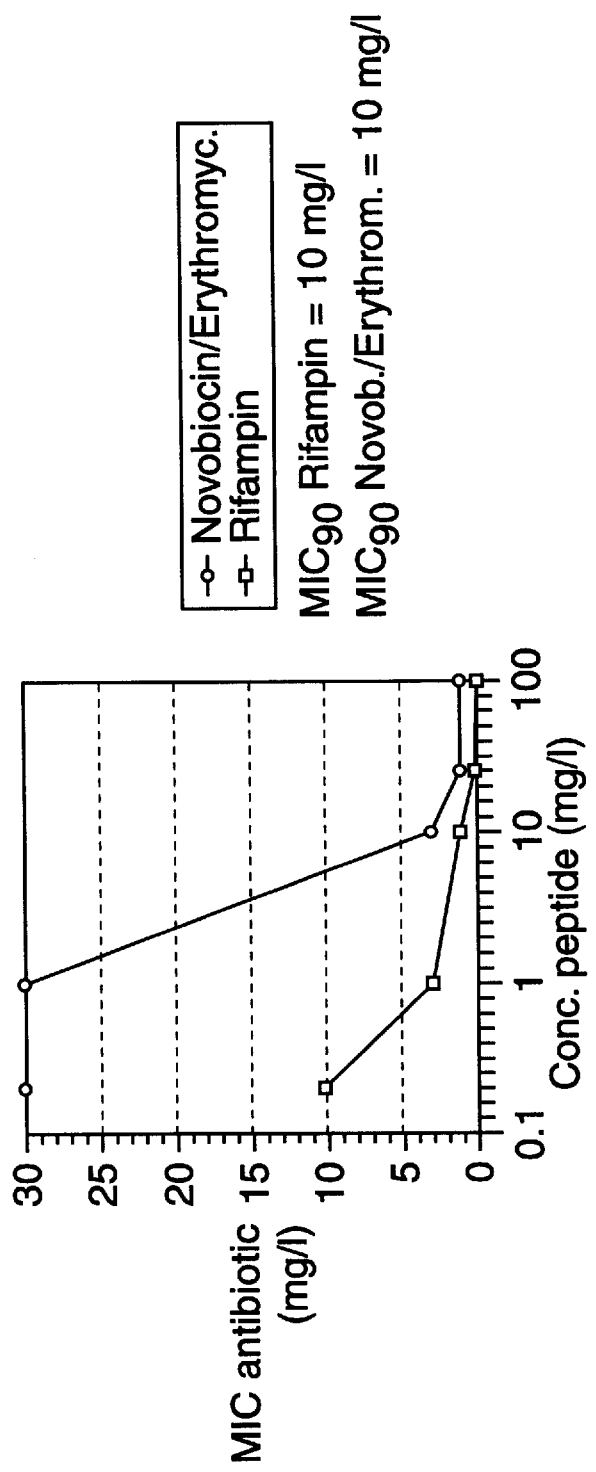
FIG. 1 graphically shows the effect of the peptide identified herein by Sequence ID No.:31 on the potentiation of rifampin and a combination of novobiocin and erythromycin on *Escherichia coli* IH3080 (clinical isolate).

The peptides of the invention have not exhibited any growth inhibitory activity against bacteria when they have been used in the absence of an antibiotic substance. The ability of the peptides to potentiate the activity of antibiotics was therefore unexpected. The inventors do not wish to be bound by any theory by which the invention may be explained but it is believed that the peptides of the invention interact with the membrane of pathogenic bacteria, particularly the outer membrane of gram-negative bacteria which contains LPS. The interaction of the peptide and the LPS of the bacterial outer membrane is believed to increase the permeability of the membrane to antibiotics, particularly hydrophobic/lipophilic antibiotics.

The term antibiotic is used according to Tabers Cyclopedic Medical Dictionary, 15th Ed. to describe antimicrobial substances which have the ability to inhibit the growth of or to destroy microorganisms. These substances are active in dilute solutions and may be produced in whole or in part by a microorganism or by a synthetic or semi-synthetic method.

Antibiotics which are useful in the present invention include penicillin derivatives such as penicillin G, penicillin V, penicillin G benzathine, ampicillin, amoxacillin, nafcillin, carbenicillin, dicloxacillin, bacampicillin, piperacillin, ticaricillin, mezlocillin and the like; cephalosporins such as cefazolin, cefadroxil, cephalexin, cefaclor, cefoxitin, cefonicid, ceftizoxime, cefprozil, ceftazidine, cefixime, cefpodoxime proxitel and the like; aminoglycosides such as amikacin, gentamicin, tobramycin, netilmicin, streptomycin and the like; macrolides such as erythromycin and the like; monobactams such as aztreonam and the like; rifamycin and derivatives such as rifampin, rifamide, rifaximin and the like; chloramphenicol; clindamycin; lincomycin; imipenem; vancomycin; tetracyclines such as chlortetracycline, tetracycline, minocycline, doxycycline and the like; fusidic acid; novobiocin and the like; fosfomycin, fusidate sodium, neomycin, bacitracin, polymyxin, capreomycin, colistimethate, colistin and gramicidin.

In addition, a peptide may be used with one antibiotic or it may be used in combination with more than one antibiotic and/or in combination with other antibacterial agents. Suitable combinations include:

rifampin+erythromycin
erythromycin+sulfonamide such as sulfisoxazole
penicillin+streptomycin
rifampin+beta lattamin
rifampin+fluoroquinolones
rifampin+vancomycin
rifampin+tetracyclines
rifampin+trimetoprim
novobiocin+fluoroquinolones
trimetoprim+sulfonamides
rifampin+fusidic acid
rifampin+isoniazid
rifampin+fosfomycin
rifampin+clofazmin+dapsone rifampin+aminoside
vancomycin+fusidic acid Many of the antimicrobial drugs are described in Remingtons Pharmaceutical Sciences, 15th Ed., Chapter 64, which is incorporated by reference.

The peptides which are useful for potentiating the activity of antibiotics are linear or cyclic peptides having units of the formula:

(a) $(A)_n$ wherein A is Lysine or Arginine and n is an integer with a minimum value of 7;

(b) $(AB)_m$ wherein A is Lysine or Arginine and B is a hydrophobic amino acid selected from the group consisting of Valine, Leucine, Isoleucine, Tyrosine, Phenylalanine and Tryptophan; m is an integer with a minimum value of 3; and (c) $(ABC)_p$ wherein A is a cationic amino acid which is Lysine or Arginine; B and C are hydrophobic amino acids which may be the same or different and are selected from the group consisting of Valine, Leucine, Isoleucine, Tyrosine, Phenylalanine and Tryptophan; p is an integer with a minimum value of 2. The peptides of the invention may be terminated independently with a hydrogen atom or any of the naturally occurring amino acids, a fatty acid residue or a carbohydrate residue. In addition the retroinverted peptides of the peptides described herein may also be employed.

The preferred peptides for use in the invention will also have a ratio of aliphatic cationic amino acids to hydrophobic amino acids ($R_{c/h}$) of at least 0.5 and within the range of about 0.5 to 10.0 which is computed by using the solvent parameter values only for those amino acids which are present in the peptides which have a solvent parameter value equal to or greater than +1.5kcal/mol (lysine and arginine) and −1.5kcal/mol (valine, isoleucine, leucine, tryrosine, phenylalanine and tryptophane) as measured according to Levitt, J. Mol. Biol. 104,59 (1976), which is incorporated by reference.

The minimal effective peptide sequence for use in potentiating an antibiotic comprises six to seven amino acid residues containing a minimum of three aliphatic cationic amino acids, with a ratio of aliphatic cationic amino acids to hydrophobic amino acids of equal to or greater than 0.5 ($R_{c/h}$ wherein c is the number of cationic amino acids in the peptide and h is the number of hydrophobic amino acids in the peptide). This ratio is believed to be the minimum although sequences of ten amino acids with a ratio ($R_{c/h}$) equal to or greater than 1.0 are optimal for expression of biological activity.

The peptide units which are represented by formula (a), (b) and (c) represent discrete peptides which will potentiate antibiotics have specific formulas which are identical with the units of formula (a), (b) and (c) as well as peptides which will bind endotoxin in the LAL inhibition test and which include as a part of their structure units of formula (a), (b) and (c), in addition to other amino acids, are included within the peptides which comprise the invention.

The peptides should not exhibit hemolytic activity when equal volumes of a solution of the peptide in isotonic saline, at a minimum peptide concentration of 0.1 mg/ml and a solution of 10%w/w fresh human erythrocytes in isotonic saline are incubated at 37° C. for 30 minutes and no rupture of the erythrocytes and release of hemoglobin is detected visually or by use of a spectrophotometer (540 nm).

The minimum values for n, m and p have been determined experimentally on the basis of the observation that when the peptide is linear, it will have at least 7 amino acid units and when said peptide is cyclic or a polymer having several cycles, i.e. 2 to 6 cycles, it will have a ring structure that has a minimum of 6 amino acid units and preferably a maximum of 7 amino acid units; said peptides having a ratio of aliphatic cationic amino acids to hydrophobic amino acids which is equal to or greater than 0.5.

When the peptides are of the formula $(A)_n$, $(AB)_m$ or $(ABC)_p$, i.e. when these formulas do not represent units of a larger peptides, n will be from 7 to 500 and preferably from 7 to 10; m will be from 3 to 200 and preferably from 4 to 20 and p will be from 2 to 100 and preferably from 4 to 20.

Examples of the peptides are listed below. Those peptides which are not novel are marked by an asterisk:

$(Lys)_{10}$ (SEQ ID NO: 1);
$(Lys)_{30}$* (SEQ ID NO: 2);
$(Lys)_{434}$* (SEQ ID NO: 3);
$(Lys-Asp)_5$ (SEQ ID NO: 4);
$(Lys-Phe)_5$ (SEQ ID NO: 5);
Lys—Phe—Leu—Lys—Lys—Thr—Leu (SEQ ID NO: 6);
$(Lys-Phe-Leu)_2-Lys$ (SEQ ID NO: 7);
$(Lys-Phe-Leu)_3-Lys$ (SEQ ID NO: 8);
$(Arg-Tyr-Val)_3$ (SEQ ID NO: 9);
$(Lys-Phe-Phe)_3-Lys$ (SEQ ID NO: 10);
$(Lys-Leu-Leu)_3$ (SEQ ID NO: 11);
$(Lys)_6(Phe-Lys)_2$ (SEQ ID NO: 12);
Cys—$(Lys)_5$—Cys
s----------s (SEQ ID NO: 13);

Cys—Lys—Phe—Lys—Lys—Cys
s------------------------s (SEQ ID NO: 14);

Lys—Phe—Lys—Cys—Lys—Phe—Lys—Phe—Lys—Cys
          s----------------------------s
(SEQ ID NO: 15);
Lys—Leu—Lys—Cys—Lys—Leu—Lys—Leu—Lys—Cys
          s----------------------------s
(SEQ ID NO: 16);
Arg—Thr—Arg—Cys—Arg—Phe—Lys—Arg—Arg—Cys
          s----------------------------s
(SEQ ID NO: 17);
Lys—Cys—$(Lys-Phe-Lys)_2$—Cys—Lys
      s---------------------s (SEQ ID NO: 18);
Cys—$(Lys)_4$—$(Phe)_4$—Cys
s-------------------s (SEQ ID NO: 19);

Cys—$(Lys-Phe-Leu)_3$—Lys—Cys
s--------------------------s (SEQ ID NO: 20);

Val—Lys—Ala—Leu—Arg—Val—Arg—Arg—Leu (SEQ ID NO: 21);
Lys—Ser—Leu—Ser—Leu—Lys—Arg—Leu—Thr—Tyr—Arg (SEQ ID NO: 22);
Lys—Val—Arg—Lys—Ser—Phe—Phe—Lys—Val (SEQ ID NO: 23);
Phe—Leu—Lys—Pro—Gly—Lys—Val—Lys—Val (SEQ ID NO: 24);
Lys—Asp—Leu—Lys—Arg—Ile—Lys—Ile (SEQ ID NO: 25);
Lys—Trp—Lys—Ala—Gln—Lys—Arg—Phe—Leu (SEQ ID NO: 26);
Lys—Trp—Lys—Ala—Gln—Lys—Arg—Phe—Leu—Lys (SEQ ID NO: 27);
Lys—Arg—Leu—Lys—Trp—Lys—Tyr—Lys—Gly—Lys—Phe (SEQ ID NO: 28);
and
Cys—Gln—Trp—Lys—Ser—Ser—Asp—Ile—Arg—Cys—Gly—Lys
s----------------------------------------s
(SEQ ID NO: 29).
Cys—Lys—Phe—Leu—Lys—Lys—Cys
s--------------------------s (SEQ ID NO: 30)

Lys—Thr—Lys—Cys—Lys—Phe—Leu—Lys—Lys—Cys
          s----------------------------s
(SEQ ID NO: 31)
Lys—Phe—Leu—Lys—Lys—Thr (SEQ ID NO: 32)
Cys—Lys—Lys—Leu—Phe—Lys—Cys—Lys—Thr—Lys
s----------------------------s (SEQ ID NO: 33)
Cys—Lys—Lys—Leu—Phe—Lys—Cys—Lys—Thr
s--------------------------s (SEQ ID NO: 34)
Ile—Lys—Thr—Lys—Cys—Lys—Phe—Leu—Lys—Lys—Cys
              s----------------------------s
(SEQ ID NO: 35)
Ile—Lys—Thr—Lys—Lys—Phe—Leu—Lys—Lys—Thr
(SEQ ID NO: 36)
Ile—Lys—Phe—Leu—Lys—Phe—Leu—Lys—Phe—Leu—Lys
(SEQ ID NO: 37)
Lys—Phe—Leu—Lys—Phe—Leu—Lys (SEQ ID NO: 38)

-continued
Arg—Tyr—Val—Arg—Tyr—Val—Arg—Tyr—Val (SEQ ID NO: 39)
Lys—Phe—Phe—Lys—Phe—Phe—Lys—Phe—Cys (SEQ ID NO: 40)
Ile—Lys—Phe—Leu—Lys—Phe—Leu—Lys—Phe—Leu
(SEQ ID NO: 41)
(Lys)⁶Phe—Leu—Phe—Leu (SEQ ID NO: 42)
Cys—Lys—Phe—Lys—Phe—Lys—Phe—Lys—Phe—Cys
s------------------------------------------s
(SEQ ID NO: 43)
Lys—Trp—Lys—Ala—Gln—Lys—Arg—Phe—Leu—Lys
(SEQ ID NO: 44)
Lys—Arg—Leu—Lys—Trp—Lys—Tyr—Lys—Gly—Lys—Phe
(SEQ ID NO: 45)

The peptides for use in the present invention may be synthesized by classical methods of peptide chemistry using manual or automated techniques as well as by DNA recombinant technology. The synthetic procedure comprises solid phase synthesis by Fmoc chemistry, cleavage (TFA 95%+ Et-(SH)$_2$ 5%), followed by vacuum evaporation. Thereafter, the product is dissolved in 10% acetic acid, extracted with ether, concentrated at 0.1 mg/ml at pH of 6.0–7.5. Stirring under filtered air followed for 1 to 6 hours in case of the Cysteine-containing peptides and finally desalting by reverse phase chromatography is carried out.

A particular automated method of preparing peptides for use in the present invention is based on the use of an automatic synthesizer (Milligen Mod.9050 (MILLIPORE, Burlington, Mass.) on a solid phase support of polyamide/Kieselguhr resin (2.0 g). The amino acids used in the synthesis of the peptide analogs are Fmoc-aa-Opfp derivatives (9-Fluorenylmethylcarbonyl-aa-O-pentafluorophenyl ester) of each amino acid(aa) involved in the considered sequences using 0.8 mol of each amino acid to sequentially form the peptide.

Each cycle of synthesis may be performed at room temperature (20° C.) and involves the following steps of reaction:

Step 1—Deprotection

The first aa Fmoc-protected at the amino group, was treated with a 20% solution of piperidine for 7 minutes in order to remove the Fmoc alpha-protecting group. Washing with dimethylformamide followed for 12 minutes to remove all traces of piperidine. Deprotection and washing were run continuously through the column containing the resin by means of a pump at a flow of 5 ml/min.

Step 2—Activation of the Fmoc-aa-Opfp derivative

The amino and carboxy-protected amino acid due, according to the desired sequence, was activated after its dissolution in 5 ml of dimethylformamide, by a catalytic amount of hydroxybenzotriazol (0.5 ml of a 5% w/v solution in dimethylformamide).

Step 3—Acylation

The activated and protected Fmoc-aa-Opfp derivative was then recycled for 30 minutes through the column by the pump at 5 ml/min in order to obtain coup[ling of the introduced aa at the alpha-amino group (previously deprotected as reported in Step 1) of the amino acid preceding the new one in the desired sequence.

Step 4—Washing

Washing of the matrix in the column followed by dimethylformamide for 2 minutes at 5 ml/min before a new cycle began.

At the completion of the synthesis, the peptide on the resin support was cleaved by 95% Trifluoroacetic acid (TFA) with 5% Ethane dithiol as a scavenger, if Cysteine residues were present in the aa sequence, at room temperature for 2 hours. After separation of the cleaved peptide from the resin by filtration, the solution was concentrated by vacuum evaporation to dryness. The collected solid residue was then solubilized in 10% acetic acid at a concentration of 10–20 mg/ml and several extractions by diethyl ether followed (six to eight extractions with half the volume of the peptide solution) in order to remove the scavenger Ethane dithiol. The peptide solution was then neutralized by 0.1N ammonium hydroxide and adjusted to the concentration of roughly 0.1 mg/ml. The solution was then stirred under air for 1 to 6 hours in order to obtain the selective oxidation of the two sulfhydryl groups belonging to the Cys residues of the sequence. In this way, only monomeric oxidized peptides were obtained with no traces of polymeric material. The solution of oxidized peptide was then desalted by reverse-phase chromatography on SEP-PAK C-18 cartridges (MILLIPORE) and finally freeze dried. The products were analyzed by high-performance liquid chromatography (HPLC) analysis as well as by chemical analysis of the synthetic structures.

Fast atom bombardment may be used to confirm the calculated mass of the peptides.

The peptides described herein which exhibit the absence or a low level of hemolysis may be used in the treatment of infections in mammals including humans at doses of about 0.1 mg–2.0 mg/kg of body weight or may be used at a level of about 0.2 mg to about 1.0 mg/kg of body weight and the amount may be administered in divided doses on daily basis prior to, simultaneously with or after the administration of an antibiotic. Generally the doses of the antibiotic will be reduced by from about 90% to about 10% of the standard therapeutic dose of a given antibiotic as shown in standard compendia such as the 1994 Physicians Desk Reference, which is incorporated by reference. The combination of the peptide and the antibiotic may be administered prophylactically to patients who may be exposed to or have been exposed to organisms which may cause infection. The particular dose of a particular peptide with a particular antibiotic may be varied within or without the range that is specified herein depending on the particular application or severity of the infection and the condition of the host. Those who are skilled in the art may ascertain the proper dose using standard procedures. A convenient dose of a combined formulation of the peptide and the antibiotic may be 0.1–1.0 mg/Kg of body weight of peptide with 0.25–40 mg/Kg of body weight of antibiotic administered daily in single or multiple doses in order to achieve and maintain therapeutic plasma concentrations.

The peptides may be administered intravenously and parenterally using well known pharmaceutical carriers or inert diluents and the antibiotics may be administered intravenously, parenterally or orally depending on the particular antibiotic. Aqueous, physiologically compatible diluents are preferred. A composition containing both the peptide and the antibiotic may be placed in the same sterile container for dilution with a suitable diluent such as sterile isotonic saline or sterile water for injection prior to administration. If the peptide and the antibiotic are not compatible, they may be placed in containers that provide a means for separation of the components until just prior to use or they may be placed in separate containers. The invention also includes topical preparations containing the peptide and antibiotic in the form of ophthalmic ointments or drops; otological preparations such as viscous liquids e.g. propylene glycol based sterile solutions or dispersions; and topical creams and ointments for the treatment and/or prevention of skin infections. Suitable vehicles and the techniques for preparing suitable vehicles are set forth in Remingtons Pharmaceutical Sciences, 17th Ed., Mack Pub. Co., Easton, Pa. 18042, Chapters 84, 87 and 88, which is incorporated by reference. Generally the concentration of the peptide and the antibiotic in these preparations will be sufficient to exert an antimicrobial effect. These amounts will vary depending on the particular drugs which are selected and may be determined by routine experimentation. Generally the peptides may be used at a concentration of 0.1–5 wt % and the antibiotics may be used at from 90% to 10% of the usual therapeutic amount.

When other antibacterial agents are used in combination with an antibiotic and the peptide composition, the total amount of the antibacterial may also be reduced from 10 to 90% while still obtaining an enhanced therapeutic response with reduced toxicity.

DESCRIPTION OF THE PREFERRED EMBODIMENTS

Example 1

Figure 2:
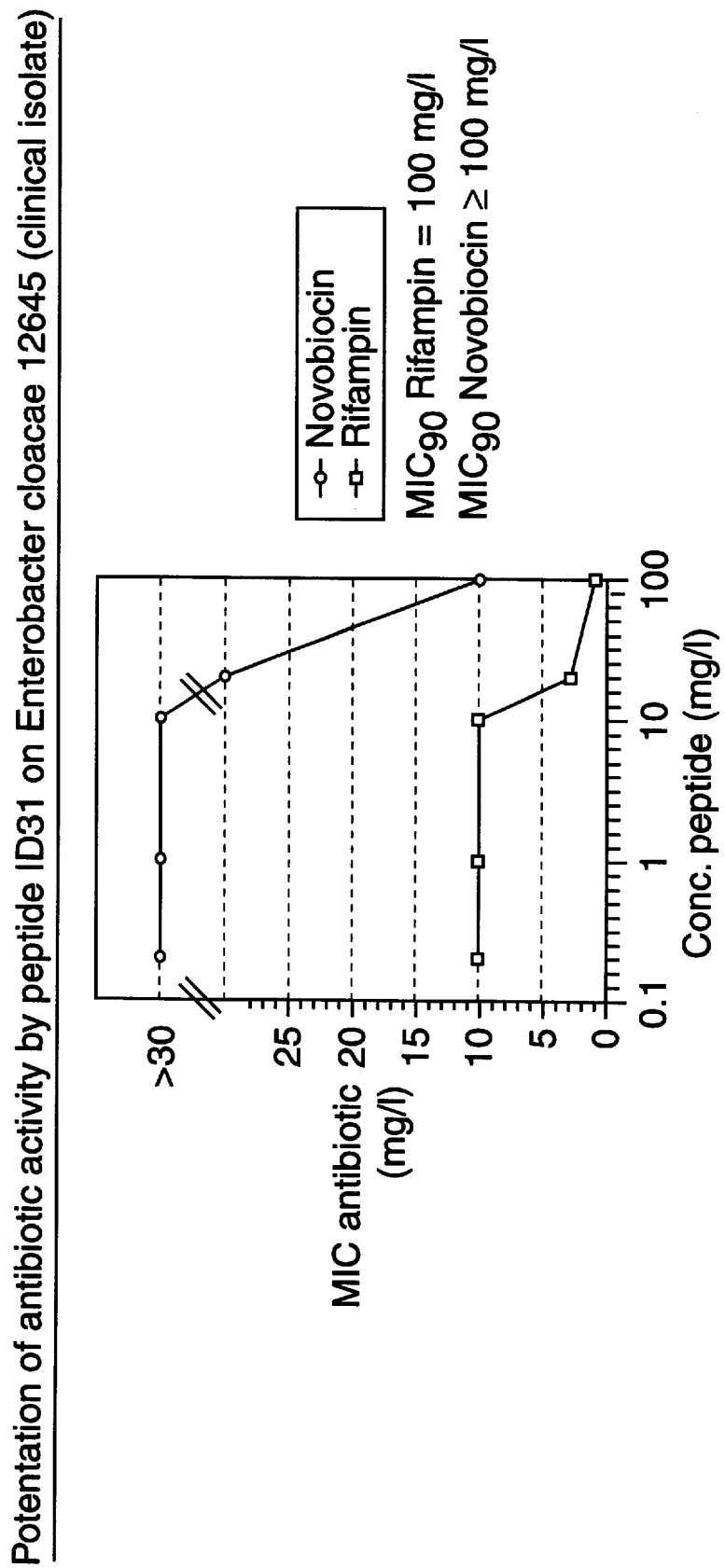
FIG. 2 graphically shows the effect of the peptide identified herein by Sequence ID No.:31 on the potentiation of rifampin and novobiocin on *Enterobacter cloacae* 12645 (clinical isolate).
Figure 3:
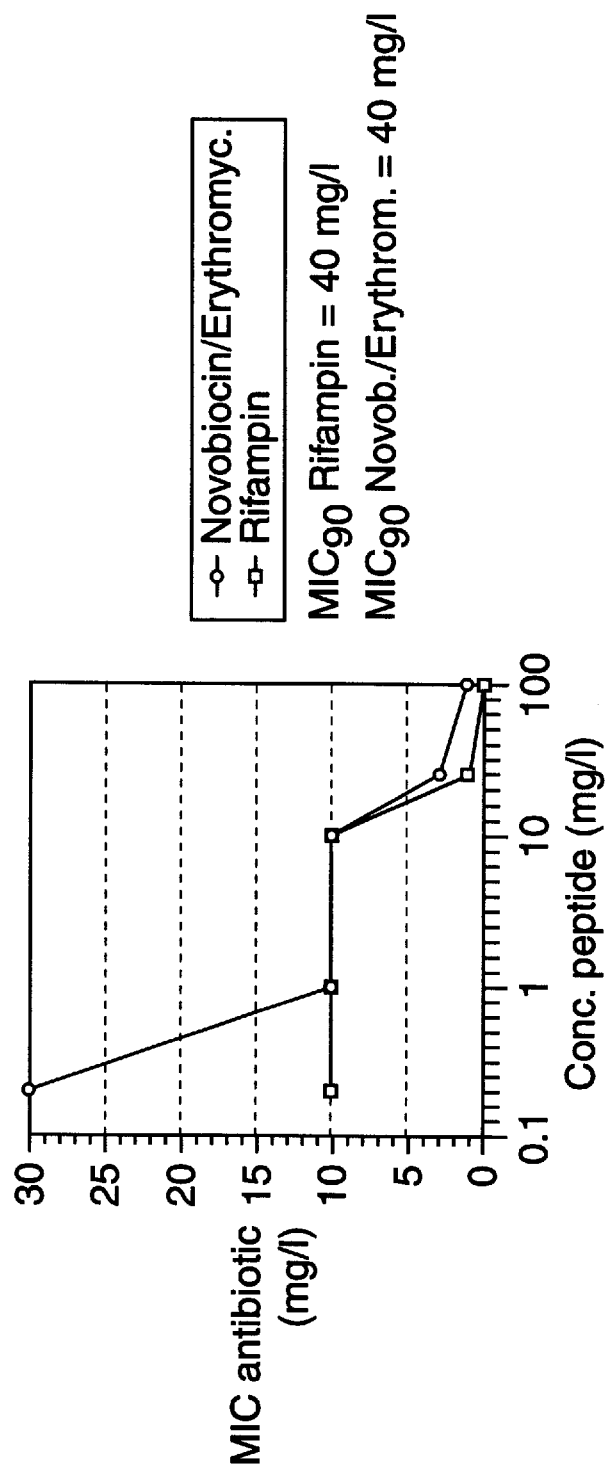
FIG. 3 graphically shows the potentiation of antibiotic activity of the peptide identified herein by Sequence ID NO.: 31 on the potentiation of rifampin and a combination of novobiocin and erythromycin on *Salmonella typhimurium* SH5014.
Figure 4:
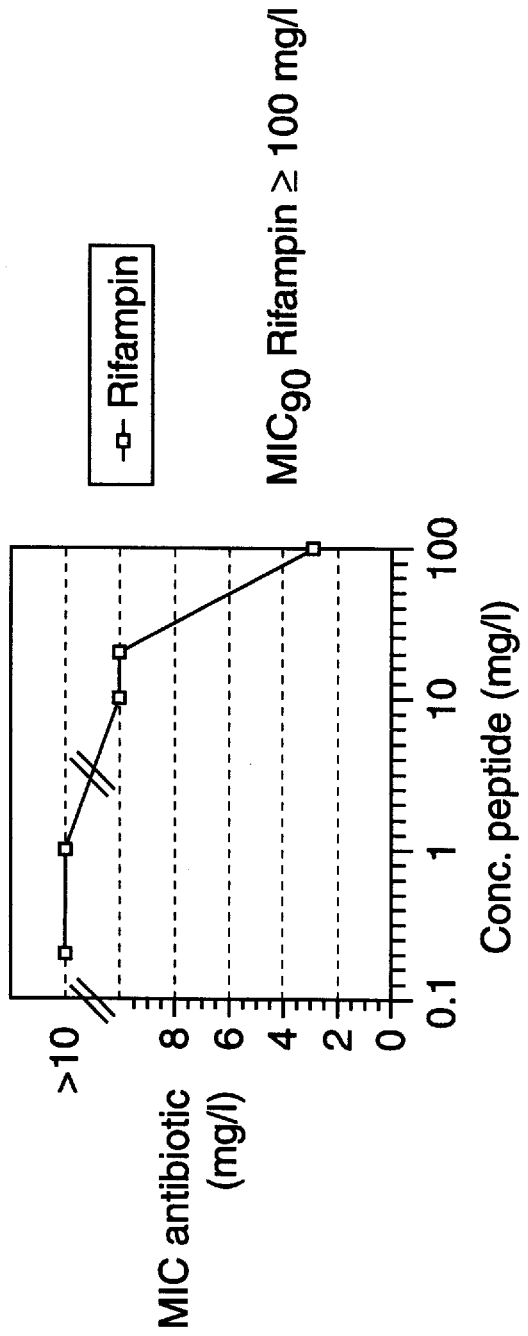
FIG. 4 graphically shows the potentiation of antibiotic activity of the peptide identified herein by Sequence ID NO.: 31on the potentiation of rifampin on *Pseudomaonas aeruginosa* PA01 (clinical isolate).
Figure 5:
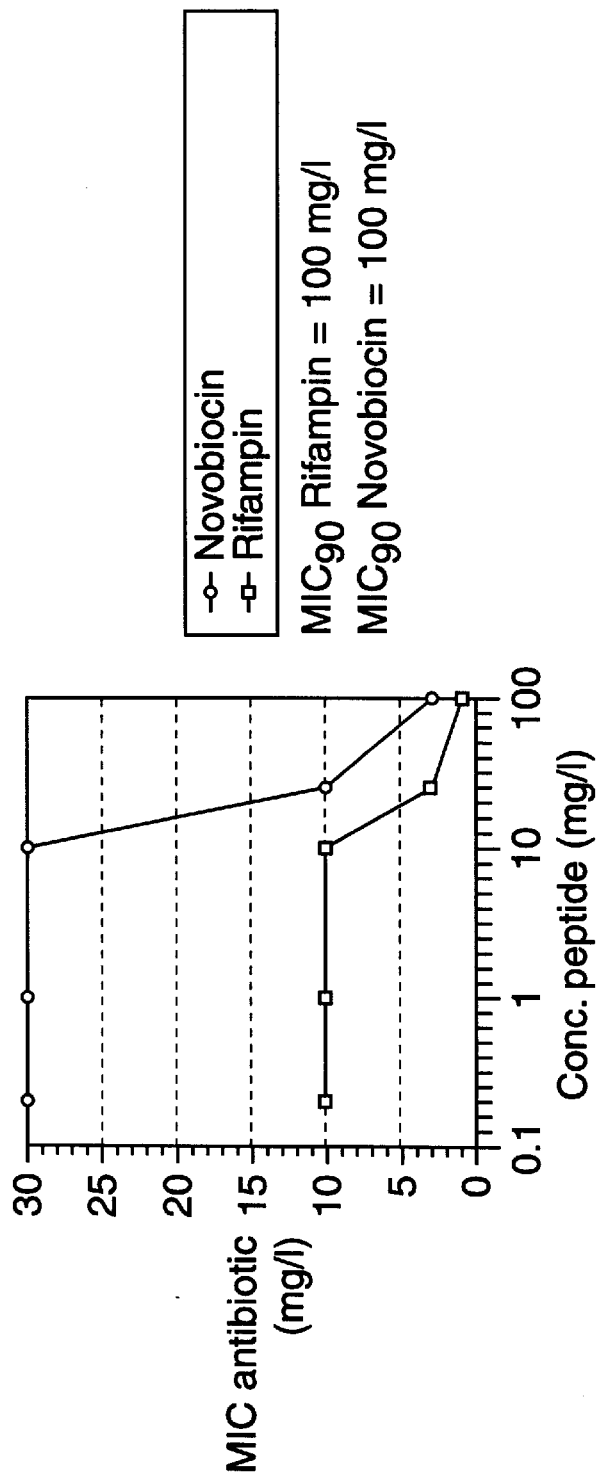
FIG. 5 graphically shows the potentiation of antibiotic activity of the peptide identified herein by Sequence ID NO.: 31 on the potentiation of novobiocin and rifampin on *Klebsiella pneumoniae* 12854 (clinical isolate).

The growth inhibition of the combination of a peptide and an antibiotic was demonstrated in vitro using microdilution plates, the checkerboard technique and a bacterial inoculum size of $10^4$ bacterial cells/ml. The general assay medium was L broth (pH7.2) which contained 10 g of tryptone (Difco Laboratories, Detroit, Mich.), 5 g of yeast extract (Oxoid Ltd., Hampshire, UK) and 5 g of sodium chloride per liter. After an incubation time of 18 hours at 37° C., the growth of each microtiter well is measured with a Titerteck Multiscan spectrophotometer at 405 nm. Before reading, the spectrophotometer was blanked with corresponding uninoculated drug-containing media. The minimum inhibitory concentration (MIC) of an antibiotic was defined as the lowest concentration of the antibiotic expressed in mg/l which reduced the growth of the target bacteria by ≧90% ($MIC_{90}$). The results of the MIC tests show that the combination of an antibiotic and a peptide provides synergistic growth inhibition activity. These results are summarized in Table I and are shown specifically for a representative peptide in FIG. 1 and FIG. 2.

TABLE I

| Peptide Seq. ID | Concentration of peptide (mg/1) | E. coli IH3080 Experiment I MIC Rifampin | E. coli IH3080 Experiment II MIC Fusidic a. |
|---|---|---|---|
| None | 0 | 10 | 300 |
| 30 | 1 | 10 | 300 |
|  | 10 | 3 | 300 |
|  | 100 | 0.1 | 10 |
| 31 | 1 | 3 | 300 |
|  | 10 | 1 | 100 |
|  | 100 | 0.1 | 10 |
| 35 | 1 | 10 | 300 |
|  | 10 | 3 | 100 |
|  | 100 | 1 | 100 |
| 40 | 1 | 1 | 100 |
|  | 10 | 0.03 | 1 |
| 41 | 1 | 1 | 100 |
|  | 10 | 0.03 | 1 |
|  | 30 | 0.01 | 1 |

| Peptide Seq, ID | Concentration of peptide (mg/1) | E. coli IH3080 Experiment III MIC Novobiocin | E. coli IH3080 Experiment IV MIC Erythrom. |
|---|---|---|---|
| None | 0 | 30 | 30 |
| 30 | 1 | 30 | 30 |
|  | 10 | 10 | 30 |
|  | 100 | 1 | 1 |
| 31 | 1 | 30 | 30 |
|  | 10 | 3 | 10 |
|  | 100 | 1 | 1 |

TABLE I-continued

| | | | |
|---|---|---|---|
| 35 | 1 | 30 | 30 |
|  | 10 | 30 | 30 |
|  | 100 | 3 | 30 |
| 40 | 1 | 1 | 30 |
|  | 10 | 1 | 3 |
|  | 30 | 1 | 1 |
| 41 | 1 | 10 | 10 |
|  | 10 | 1 | 1 |

| Peptide Seq. ID | Concentration of peptide (mg/1) | E. coli IH3080 Experiment I MIC Rifampin | E. coli IH3080 Experiment II MIC Fusidic a. |
|---|---|---|---|
| 42 | 1 | 10 | 300 |
|  | 10 | 3 | 300 |
| 43 | 1 | 10 | 300 |
|  | 10 | 1 | 100 |
|  | 30 | 0.1 | 10 |
| 26 | 1 | 10 | 300 |
|  | 10 | 1 | 300 |
|  | 100 | 0.3 | 30 |
| 28 | 1 | 1 | 300 |
|  | 10 | 0.3 | 100 |
|  | 100 | 0.01 | 1 |

| Peptide Seq. ID | Concentration of peptide (mg/1) | E. coli IH3080 Experiment III MIC Novobiocin | E. coli IH3080 Experiment IV MIC Erythrom. |
|---|---|---|---|
| 42 | 1 | 10 | 100 |
|  | 10 | 10 | 30 |
| 43 | 1 | 30 | 100 |
|  | 10 | 10 | 30 |
|  | 30 | 1 | 1 |
| 26 | 1 | 30 | 30 |
|  | 10 | 10 | 30 |
|  | 100 | 3 | 10 |
| 28 | 1 | 10 | 30 |
|  | 10 | 3 | 10 |
|  | 100 | 1 | 1 |

| Peptide Seq. ID | Concentration of peptide (mg/1) | S. typhi SH5014 Experiment I MIC Rifampin | S. typhi SH5014 Experiment II MIC Fusidic a. |
|---|---|---|---|
| None | 0 | 10 | >300 |
| 30 | 1 | 10 | >300 |
|  | 10 | 10 | >300 |
|  | 100 | 0.1 | 30 |
| 31 | 1 | 10 | >300 |
|  | 10 | 10 | >300 |
|  | 100 | 0.03 | 3 |
| 35 | 1 | 10 | >300 |
|  | 10 | 10 | >300 |
|  | 100 | 3 | 300 |
| 40 | 1 | 3 | 100 |
|  | 10 | 0.01 | 1 |
| 41 | 1 | 3 | 100 |
|  | 3 | 0.01 | 1 |

| Peptide Seq. ID | Concentration of Peptide (mg/ml) | S. typhi SH5014 Experiment III MIC Novobiocin | S. typhi SH5014 Experiment IV MIC Erythromycin. |
|---|---|---|---|
| None | 0 | 30 | 100 |
| 30 | 1 | 30 | 100 |
|  | 10 | 30 | 100 |
|  | 100 | 1 | 10 |
| 31 | 1 | 10 | 100 |
|  | 10 | 10 | 100 |
|  | 100 | 1 | 3 |
| 35 | 1 | 30 | 100 |
|  | 10 | 10 | 100 |
|  | 100 | 10 | 100 |
| 40 | 1 | 10 | 100 |
|  | 10 | 1 | 1 |
| 41 | 1 | 10 | 100 |
|  | 3 | 1 | 1 |

TABLE I-continued

| Peptide Seq. ID | Concentration of peptide (mg/l) | S. typhi SH5014 Experiment I MIC Rifampin | S. typhi SH5014 Experiment II MIC Fusidic a. |
|---|---|---|---|
| 42 | 1 | 10 | >300 |
|  | 10 | 10 | 300 |
| 43 | 1 | 10 | >300 |
|  | 10 | 3 | 300 |
|  | 30 | 0.1 | 1 |
| 26 | 1 | 10 | >300 |
|  | 10 | 3 | 100 |
|  | 100 | 0.3 | 30 |
| 28 | 1 | 10 | 300 |
|  | 10 | 1 | 300 |
|  | 30 | 0.1 | 100 |

| Peptide Seq. ID | Concentration of peptide (mg/l) | S. typhi. SH5014 Experiment III MIC Novobiocin | S. typhi. SH5014 Experiment IV MIC Erythrom. |
|---|---|---|---|
| 42 | 1 | 30 | 100 |
|  | 10 | 10 | 100 |
| 43 | 1 | 30 | 100 |
|  | 10 | 10 | 100 |
|  | 30 | 1 | 1 |
| 26 | 1 | 30 | 100 |
|  | 10 | 10 | 100 |
|  | 100 | 3 | 30 |
| 28 | 1 | 10 | 100 |
|  | 10 | 3 | 100 |
|  | 30 | 1 | 10 |

| Peptide Seq. ID | Concentration of peptide (mg/l) | Ps. aeroginosa. PAO1 Experiment I MIC Rifampin | Ps. aeroginosa. PAO1 Experiment II MIC Fusidic a. |
|---|---|---|---|
| None | 0 | >10 | >300 |
| 30 | 1 | >10 | >300 |
|  | 10 | >10 | >300 |
|  | 100 | 10 | >300 |
| 31 | 1 | >10 | >300 |
|  | 10 | 10 | >300 |
|  | 100 | 3 | 300 |

| Peptide Seq. ID | Concentration of peptide (mg/l) | Ps. aeroginosa. PAO1 Experiment III MIC Novobiocin | Ps. aeroginosa. PAO1 Experiment IV MIC Erythrom. |
|---|---|---|---|
| None | 0 | >30 | 100 |
| 30 | 1 | >30 | 100 |
|  | 10 | >30 | 100 |
|  | 100 | >30 | 100 |
| 31 | 1 | >30 | 100 |
|  | 10 | >30 | 100 |
|  | 100 | >30 | 100 |

| Peptide Seq. ID | Concentration of peptide (mg/l) | Kl. pneumoniae 12854 Experiment I MIC Rifampin | Kl. pneumoniae 12854 Experiment II MIC Fusidic a. |
|---|---|---|---|
| None | 0 | 10 | >300 |
| 30 | 1 | 10 | >300 |
|  | 10 | 10 | >300 |
|  | 100 | 1 | 100 |
| 31 | 1 | 10 | >300 |
|  | 10 | 10 | 300 |
|  | 100 | 1 | 30 |
| 35 | 1 | 10 | >300 |
|  | 10 | 10 | >300 |
|  | 100 | 10 | 300 |
| 40 | 1 | 10 | 100 |
|  | 10 | 0.1 | 10 |
|  | 100 | 0.01 | 1 |
| 41 | 1 | 3 | 300 |
|  | 10 | 0.03 | 3 |
|  | 30 | 0.01 | 1 |

| Peptide Seq. ID | Concentration of peptide (mg/l) | Kl. pneumoniae 12854 Experiment III MIC Novobiocin | Kl. pneumoniae 12854 Experiment IV MIC Erythrom. |
|---|---|---|---|
| None | 0 | 30 | >100 |
|  | 1 | 30 | >100 |
|  | 10 | 30 | >100 |
|  | 100 | 10 | 30 |
| 31 | 1 | 30 | >100 |
|  | 10 | 30 | >100 |
|  | 100 | 3 | 30 |
| 35 | 1 | 30 | >100 |
|  | 10 | 30 | >100 |
|  | 100 | 10 | >100 |
| 40 | 1 | 30 | >100 |
|  | 10 | 3 | 3 |
|  | 100 | 1 | 1 |
| 41 | 1 | 10 | >100 |
|  | 10 | 1 | 3 |
|  | 30 | 1 | 1 |

| Peptide Seq. ID | Concentration of peptide (mg/l) | Kl. pneumoniae 12584 Experiment I MIC Rifampin | Kl. pneumoniae 12584 Experiment II MIC Fusidic a. |
|---|---|---|---|
| 42 | 1 | 10 | >300 |
|  | 10 | 10 | >300 |
|  | 100 | 1 | 100 |
| 43 | 1 | 10 | >300 |
|  | 10 | 10 | 300 |
|  | 100 | 0.3 | 30 |
| 26 | 1 | 10 | >300 |
|  | 10 | 10 | 300 |
|  | 100 | 3 | 100 |
| 28 | 1 | 10 | >300 |
|  | 10 | 10 | 300 |
|  | 100 | 1 | 30 |

| Peptide Seq. ID | Concentration of peptide (mg/l) | Kl. pneumoniae 12584 Experiment III MIC Novobiocin | Kl. pneumoniae 12584 Experiment IV MIC Erythromycin. |
|---|---|---|---|
| 42 | 1 | 30 | >100 |
|  | 10 | 30 | >100 |
|  | 100 | 1 | 10 |
| 43 | 1 | 30 | >100 |
|  | 10 | 30 | >100 |
|  | 100 | 3 | 10 |
| 26 | 1 | 30 | >100 |
|  | 10 | 30 | >100 |
|  | 100 | 10 | 100 |
| 28 | 1 | 30 | >100 |
|  | 10 | 10 | 100 |
|  | 100 | 3 | 30 |

| Peptide Seq. ID | Concentration of peptide (mg/l) | E. cloa 12645 Experiment I MIC Rifampin | E. cloa 12645 Experiment II MIC Fusidic a. |
|---|---|---|---|
| None | 0 | 10 | >300 |
| 30 | 1 | 10 | >300 |
|  | 10 | 10 | >300 |
|  | 100 | 0.3 | 30 |
| 31 | 1 | 10 | >300 |
|  | 10 | 10 | 300 |
|  | 100 | 1 | 30 |
| 35 | 1 | 10 | >300 |
|  | 10 | 10 | >300 |
|  | 100 | 3 | 300 |
| 40 | 1 | 3 | 100 |
|  | 10 | 0.1 | 3 |
|  | 100 | 0.01 | 1 |
| 41 | 1 | 3 | 100 |
|  | 10 | 0.03 | 1 |
|  | 30 | 0.01 | 1 |

TABLE I-continued

| Peptide Seq. ID | Concentration of Peptide (mg/l) | E. cloa 12645 Experiment III MIC Novobiocin | E. cloa. 12645 Experiment IV MIC Erythrom. |
|---|---|---|---|
| None | 0 | >30 | >100 |
| 30 | 1 | >30 | >100 |
|  | 10 | >30 | >100 |
|  | 100 | 10 | 30 |
| 31 | 1 | >30 | >100 |
|  | 10 | >30 | >100 |
|  | 100 | 10 | 100 |
| 35 | 1 | >30 | >100 |
|  | 10 | >30 | >100 |
|  | 100 | 30 | >100 |
| 40 | 1 | 10 | 100 |
|  | 10 | 1 | 1 |
|  | 100 | 1 | 1 |
| 41 | 1 | 30 | >100 |
|  | 10 | 1 | 1 |
|  | 30 | 1 | 1 |

| Peptide Seq. ID | Concentration of peptide (mg/l) | E. cloa 12645 Experiment I MIC Rifampin. | E. cloa 12645 Experiment II MIC Fusidic a. |
|---|---|---|---|
| 42 | 1 | 10 | >300 |
|  | 10 | 10 | >300 |
|  | 100 | 0.01 | 30 |
| 43 | 1 | 10 | >300 |
|  | 10 | 3 | >300 |
|  | 100 | 0.3 | 30 |
| 26 | 1 | 10 | >300 |
|  | 10 | 10 | >300 |
|  | 100 | 1 | 100 |
| 28 | 1 | 10 | >300 |
|  | 10 | 3 | 300 |
|  | 100 | 1 | 100 |

| Peptide Seq. ID | Concentration of peptide (mg/l) | E. cloa. 12645 Experiment III MIC Novobiocin | E. cloa. 12645 Experiment IV MIC Erythrom. |
|---|---|---|---|
| 42 | 1 | >30 | >100 |
|  | 10 | >30 | >100 |
|  | 100 | 3 | 10 |
| 43 | 1 | >30 | >100 |
|  | 10 | >30 | 100 |
|  | 100 | 10 | 10 |
| 26 | 1 | >30 | >100 |
|  | 10 | 30 | >100 |
|  | 100 | 10 | 100 |
| 28 | 1 | >30 | >100 |
|  | 10 | 30 | 100 |
|  | 100 | 10 | 100 |

The data in Table II shows that the peptides when used alone have no significant antibacterial activity. These data were obtained using the general procedure set forth above:

TABLE II

|  | Peptide SEQ ID NO: | | | | |
|---|---|---|---|---|---|
| Bacterial strain | 30 | 31 | 35 | 40 | 41 |
| E. coli IH3080 | >100 | >100 | >100 | 100 | 30 |
| S. Typhimurium SH5014 | >100 | >100 | >100 | 30 | 30 |
| Klebs pneum. 12854 | >100 | >100 | >100 | >100 | 100 |
| Enterob. cloacae 12654 | >100 | >100 | >100 | >100 | 100 |
| Pseud. aeroginosa PAO1 | >100 | >100 | >100 | 30 | 30 |
| E. coli SM 101 | >100 | >100 | >100 | 30 | 10 |
| Micrococcus luteus ML36 | 100 | 100 | >100 | 10 | 30 |

|  | Peptide SEQ ID NO: | | | |
|---|---|---|---|---|
|  | 42 | 43 | 26 | 28 |
| E. coli IH3080 | 30 | 100 | >100 | >100 |
| S. Typhimurium SH5014 | 30 | 100 | >100 | 100 |
| Klebs pneum. 12854 | >100 | >100 | >100 | >100 |
| Enterob. cloacae 12654 | >100 | >100 | >100 | >100 |
| Pseud. aeroginosa PAO1 | >100 | >100 | >100 | >100 |
| E. coli SM 101 | 30 | 30 | >100 | 100 |
| Micrococcus luteus ML36 | 10 | 30 | >100 | 30 |

Example

A human patient suffering from an infection caused by K. pneumoniae may be treated with a combination of Rifampin (0.5 mg/Kg of body weight/IV every 8 hours in normal saline) and Lys-Thr-Lys-Cys-Lys-Phe-Leu-Lys-Lys-Cys s-----------------------s (SEQ ID No.:31) (1 mg/Kg of body weight/IV every 8 hours in normal saline). The dose of Rifampin is 10 to 20% by weight of the usual clinical dose of Rifampin which is administered as the sole therapeutic agent. This reduces the possibility of any toxic side effects of Rifampin without reduction of the clinical efficacy of Rifampin.

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
( A ) LENGTH: 10 amino acids
( B ) TYPE: amino acid
( C ) TOPOLOGY: circular ( i i ) SEQUENCE DESCRIPTION: SEQ ID NO:1:

Lys Lys Lys Lys Lys Lys Lys Lys Lys Lys
1               5                   10

(2) INFORMATION FOR SEQ ID NO:2:

(i) SEQUENCE CHARACTERISTICS:
        (A) LENGTH: 30 amino acids
        (B) TYPE: amino acid
        (C) TOPOLOGY: circular (ii) SEQUENCE DESCRIPTION: SEQ ID NO:2:

```
Lys Lys Lys Lys Lys Lys Lys Lys Lys Lys
 1               5                  10
Lys Lys Lys Lys Lys Lys Lys Lys Lys Lys
                15                  20
Lys Lys Lys Lys Lys Lys Lys Lys Lys Lys
                25                  30
```

(2) INFORMATION FOR SEQ ID NO:3:

(i) SEQUENCE CHARACTERISTICS:
        (A) LENGTH: 434 amino acids
        (B) TYPE: amino acid
        (C) TOPOLOGY: circular (ii) SEQUENCE DESCRIPTION: SEQ ID NO:3:

```
Lys Lys Lys Lys Lys Lys Lys Lys Lys Lys
 1               5                  10
Lys Lys Lys Lys Lys Lys Lys Lys Lys Lys
                15                  20
Lys Lys Lys Lys Lys Lys Lys Lys Lys Lys
                25                  30
Lys Lys Lys Lys Lys Lys Lys Lys Lys Lys
                35                  40
Lys Lys Lys Lys Lys Lys Lys Lys Lys Lys
                45                  50
Lys Lys Lys Lys Lys Lys Lys Lys Lys Lys
                55                  60
Lys Lys Lys Lys Lys Lys Lys Lys Lys Lys
                65                  70
Lys Lys Lys Lys Lys Lys Lys Lys Lys Lys
                75                  80
Lys Lys Lys Lys Lys Lys Lys Lys Lys Lys
                85                  90
Lys Lys Lys Lys Lys Lys Lys Lys Lys Lys
                95                 100
Lys Lys Lys Lys Lys Lys Lys Lys Lys Lys
               105                 110
Lys Lys Lys Lys Lys Lys Lys Lys Lys Lys
               115                 120
Lys Lys Lys Lys Lys Lys Lys Lys Lys Lys
               125                 130
Lys Lys Lys Lys Lys Lys Lys Lys Lys Lys
               135                 140
Lys Lys Lys Lys Lys Lys Lys Lys Lys Lys
               145                 150
Lys Lys Lys Lys Lys Lys Lys Lys Lys Lys
               155                 160
Lys Lys Lys Lys Lys Lys Lys Lys Lys Lys
               165                 170
```

| | | | | | | | | | |
|---|---|---|---|---|---|---|---|---|---|
| Lys | Lys | Lys | Lys | Lys<br>175 | Lys | Lys | Lys | Lys | Lys<br>180 |
| Lys | Lys | Lys | Lys | Lys<br>185 | Lys | Lys | Lys | Lys | Lys<br>190 |
| Lys | Lys | Lys | Lys | Lys<br>195 | Lys | Lys | Lys | Lys | Lys<br>200 |
| Lys | Lys | Lys | Lys | Lys<br>205 | Lys | Lys | Lys | Lys | Lys<br>210 |
| Lys | Lys | Lys | Lys | Lys<br>215 | Lys | Lys | Lys | Lys | Lys<br>220 |
| Lys | Lys | Lys | Lys | Lys<br>225 | Lys | Lys | Lys | Lys | Lys<br>230 |
| Lys | Lys | Lys | Lys | Lys<br>235 | Lys | Lys | Lys | Lys | Lys<br>240 |
| Lys | Lys | Lys | Lys | Lys<br>245 | Lys | Lys | Lys | Lys | Lys<br>250 |
| Lys | Lys | Lys | Lys | Lys<br>255 | Lys | Lys | Lys | Lys | Lys<br>260 |
| Lys | Lys | Lys | Lys | Lys<br>265 | Lys | Lys | Lys | Lys | Lys<br>270 |
| Lys | Lys | Lys | Lys | Lys<br>275 | Lys | Lys | Lys | Lys | Lys<br>280 |
| Lys | Lys | Lys | Lys | Lys<br>285 | Lys | Lys | Lys | Lys | Lys<br>290 |
| Lys | Lys | Lys | Lys | Lys<br>295 | Lys | Lys | Lys | Lys | Lys<br>300 |
| Lys | Lys | Lys | Lys | Lys<br>305 | Lys | Lys | Lys | Lys | Lys<br>310 |
| Lys | Lys | Lys | Lys | Lys<br>315 | Lys | Lys | Lys | Lys | Lys<br>320 |
| Lys | Lys | Lys | Lys | Lys<br>325 | Lys | Lys | Lys | Lys | Lys<br>330 |
| Lys | Lys | Lys | Lys | Lys<br>335 | Lys | Lys | Lys | Lys | Lys<br>340 |
| Lys | Lys | Lys | Lys | Lys<br>345 | Lys | Lys | Lys | Lys | Lys<br>350 |
| Lys | Lys | Lys | Lys | Lys<br>355 | Lys | Lys | Lys | Lys | Lys<br>360 |
| Lys | Lys | Lys | Lys | Lys<br>365 | Lys | Lys | Lys | Lys | Lys<br>370 |
| Lys | Lys | Lys | Lys | Lys<br>375 | Lys | Lys | Lys | Lys | Lys<br>380 |
| Lys | Lys | Lys | Lys | Lys<br>385 | Lys | Lys | Lys | Lys | Lys<br>390 |
| Lys | Lys | Lys | Lys | Lys<br>395 | Lys | Lys | Lys | Lys | Lys<br>400 |
| Lys | Lys | Lys | Lys | Lys<br>405 | Lys | Lys | Lys | Lys | Lys<br>410 |
| Lys | Lys | Lys | Lys | Lys<br>415 | Lys | Lys | Lys | Lys | Lys<br>420 |
| Lys | Lys | Lys | Lys | Lys<br>425 | Lys | Lys | Lys | Lys | Lys<br>430 |
| Lys | Lys | Lys | Lys | | | | | | |

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) TOPOLOGY: circular ( i i ) SEQUENCE DESCRIPTION: SEQ ID NO:4:

```
Lys  Asp  Lys  Asp  Lys  Asp  Lys  Asp  Lys  Asp
1                  5                           10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) TOPOLOGY: circular ( i i ) SEQUENCE DESCRIPTION: SEQ ID NO:5:

```
Lys  Phe  Lys  Phe  Lys  Phe  Lys  Phe  Lys  Phe
1                  5                           10
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) TOPOLOGY: circular ( i i ) SEQUENCE DESCRIPTION: SEQ ID NO:6:

```
Lys  Phe  Leu  Lys  Lys  Thr  Leu
1                  5
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) TOPOLOGY: circular ( i i ) SEQUENCE DESCRIPTION: SEQ ID NO:7:

```
Lys  Phe  Leu  Lys  Phe  Leu  Lys
1                  5
```

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( C ) TOPOLOGY: circular ( i i ) SEQUENCE DESCRIPTION: SEQ ID NO:8:

```
Lys  Phe  Leu  Lys  Phe  Leu  Lys  Phe  Leu  Lys
1                  5                           10
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) TOPOLOGY: circular ( i i ) SEQUENCE DESCRIPTION: SEQ ID NO:9:

```
Arg  Tyr  Val  Arg  Tyr  Val  Arg  Tyr  Val
1                  5
```

( 2 ) INFORMATION FOR SEQ ID NO:10:

(i) SEQUENCE CHARACTERISTICS:
  (A) LENGTH: 10 amino acids
  (B) TYPE: amino acid
  (C) TOPOLOGY: circular (ii) SEQUENCE DESCRIPTION: SEQ ID NO:10:

Lys Phe Phe Lys Phe Phe Lys Phe Phe Lys
1               5                   10

(2) INFORMATION FOR SEQ ID NO:11:

(i) SEQUENCE CHARACTERISTICS:
    (A) LENGTH: 9 amino acids
    (B) TYPE: amino acid
    (C) TOPOLOGY: circular (ii) SEQUENCE DESCRIPTION: SEQ ID NO:11:

Lys Leu Leu Lys Leu Leu Lys Leu Leu
1               5

(2) INFORMATION FOR SEQ ID NO:12:

(i) SEQUENCE CHARACTERISTICS:
    (A) LENGTH: 10 amino acids
    (B) TYPE: amino acid
    (C) TOPOLOGY: circular (ii) SEQUENCE DESCRIPTION: SEQ ID NO:12:

Lys Lys Lys Lys Lys Lys Phe Lys Phe Lys
1               5                   10

(2) INFORMATION FOR SEQ ID NO:13:

(i) SEQUENCE CHARACTERISTICS:
    (A) LENGTH: 11 amino acids
    (B) TYPE: amino acid
    (C) TOPOLOGY: circular (ii) SEQUENCE DESCRIPTION: SEQ ID NO:13:

Cys Lys Cys Lys Cys Lys Cys Lys Cys Lys Cys
1               5                   10

(2) INFORMATION FOR SEQ ID NO:14:

(i) SEQUENCE CHARACTERISTICS:
    (A) LENGTH: 6 amino acids
    (B) TYPE: amino acid
    (C) TOPOLOGY: circular (ii) SEQUENCE DESCRIPTION: SEQ ID NO:14:

Cys Lys Phe Lys Lys Cys
1               5

(2) INFORMATION FOR SEQ ID NO:15:

(i) SEQUENCE CHARACTERISTICS:
    (A) LENGTH: 10 amino acids
    (B) TYPE: amino acid
    (C) TOPOLOGY: circular (ii) SEQUENCE DESCRIPTION: SEQ ID NO:15:

Lys Phe Lys Cys Lys Phe Lys Phe Lys Cys
1               5                   10

(2) INFORMATION FOR SEQ ID NO:16:

(i) SEQUENCE CHARACTERISTICS:

(A) LENGTH: 10 amino acids
(B) TYPE: amino acid
(C) TOPOLOGY: circular (ii) SEQUENCE DESCRIPTION: SEQ ID NO:16:

```
Lys  Leu  Lys  Cys  Lys  Leu  Lys  Leu  Lys  Cys
1                  5                          10
```

(2) INFORMATION FOR SEQ ID NO:17:

(i) SEQUENCE CHARACTERISTICS:
(A) LENGTH: 10 amino acids
(B) TYPE: amino acid
(C) TOPOLOGY: circular (ii) SEQUENCE DESCRIPTION: SEQ ID NO:17:

```
Arg  Thr  Arg  Cys  Arg  Phe  Lys  Arg  Arg  Cys
1                  5                          10
```

(2) INFORMATION FOR SEQ ID NO:18:

(i) SEQUENCE CHARACTERISTICS:
(A) LENGTH: 10 amino acids
(B) TYPE: amino acid
(C) TOPOLOGY: circular (ii) SEQUENCE DESCRIPTION: SEQ ID NO:18:

```
Lys  Cys  Lys  Phe  Lys  Lys  Phe  Lys  Cys  Lys
1                  5                          10
```

(2) INFORMATION FOR SEQ ID NO:19:

(i) SEQUENCE CHARACTERISTICS:
(A) LENGTH: 10 amino acids
(B) TYPE: amino acid
(C) TOPOLOGY: circular (ii) SEQUENCE DESCRIPTION: SEQ ID NO:19:

```
Cys  Lys  Lys  Lys  Lys  Phe  Phe  Phe  Phe  Cys
1                  5                          10
```

(2) INFORMATION FOR SEQ ID NO:20:

(i) SEQUENCE CHARACTERISTICS:
(A) LENGTH: 12 amino acids
(B) TYPE: amino acid
(C) TOPOLOGY: circular (ii) SEQUENCE DESCRIPTION: SEQ ID NO:20:

```
Cys  Lys  Phe  Leu  Lys  Phe  Leu  Lys  Phe  Leu  Lys  Cys
1                  5                          10
```

(2) INFORMATION FOR SEQ ID NO:21:

(i) SEQUENCE CHARACTERISTICS:
(A) LENGTH: 9 amino acids
(B) TYPE: amino acid
(C) TOPOLOGY: circular (ii) SEQUENCE DESCRIPTION: SEQ ID NO:21:

```
Val  Lys  Ala  Leu  Arg  Val  Arg  Arg  Leu
1                  5
```

(2) INFORMATION FOR SEQ ID NO:22:

(i) SEQUENCE CHARACTERISTICS:
(A) LENGTH: 11 amino acids
(B) TYPE: amino acid (C) TOPOLOGY: circular (i i) SEQUENCE DESCRIPTION: SEQ ID NO:22:

Lys Ser Leu Ser Leu Lys Arg Leu Thr Tyr Arg
1               5                   10

(2) INFORMATION FOR SEQ ID NO:23:

(i) SEQUENCE CHARACTERISTICS:
    (A) LENGTH: 9 amino acids
    (B) TYPE: amino acid
    (C) TOPOLOGY: circular (i i) SEQUENCE DESCRIPTION: SEQ ID NO:23:

Lys Val Arg Lys Ser Phe Phe Lys Val
1               5

(2) INFORMATION FOR SEQ ID NO:24:

(i) SEQUENCE CHARACTERISTICS:
    (A) LENGTH: 9 amino acids
    (B) TYPE: amino acid
    (C) TOPOLOGY: circular (i i) SEQUENCE DESCRIPTION: SEQ ID NO:24:

Phe Leu Lys Pro Gly Lys Val Lys Val
1               5

(2) INFORMATION FOR SEQ ID NO:25:

(i) SEQUENCE CHARACTERISTICS:
    (A) LENGTH: 8 amino acids
    (B) TYPE: amino acid
    (C) TOPOLOGY: circular (i i) SEQUENCE DESCRIPTION: SEQ ID NO:25:

Lys Glu Leu Lys Arg Ile Lys Ile
1               5

(2) INFORMATION FOR SEQ ID NO:26:

(i) SEQUENCE CHARACTERISTICS:
    (A) LENGTH: 9 amino acids
    (B) TYPE: amino acid
    (C) TOPOLOGY: circular (i i) SEQUENCE DESCRIPTION: SEQ ID NO:26:

Lys Trp Lys Ala Gln Lys Arg Phe Leu
1               5

(2) INFORMATION FOR SEQ ID NO:27:

(i) SEQUENCE CHARACTERISTICS:
    (A) LENGTH: 10 amino acids
    (B) TYPE: amino acid
    (C) TOPOLOGY: circular (i i) SEQUENCE DESCRIPTION: SEQ ID NO:27:

Lys Trp Lys Ala Gln Lys Arg Phe Leu Lys
1               5                   10

(2) INFORMATION FOR SEQ ID NO:28:

(i) SEQUENCE CHARACTERISTICS:
    (A) LENGTH: 11 amino acids
    (B) TYPE: amino acid
    (C) TOPOLOGY: circular ( i i ) SEQUENCE DESCRIPTION: SEQ ID NO:28:

Lys Arg Leu Lys Trp Lys Tyr Lys Gly Lys Phe
1               5                   1 0

( 2 ) INFORMATION FOR SEQ ID NO:29:

( i ) SEQUENCE CHARACTERISTICS:
( A ) LENGTH: 13 amino acids
( B ) TYPE: amino acid
( C ) TOPOLOGY: circular ( i i ) SEQUENCE DESCRIPTION: SEQ ID NO:29:

Cys Gln Ser Trp Lys Ser Ser Glu Ile Arg Cys Gly Lys
1               5                   1 0

( 2 ) INFORMATION FOR SEQ ID NO:30:

( i ) SEQUENCE CHARACTERISTICS:
( A ) LENGTH: 7 amino acids
( B ) TYPE: amino acid
( C ) TOPOLOGY: circular ( i i ) SEQUENCE DESCRIPTION: SEQ ID NO:30:

Cys Lys Phe Leu Lys Lys Cys
1               5

( 2 ) INFORMATION FOR SEQ ID NO:31:

( i ) SEQUENCE CHARACTERISTICS:
( A ) LENGTH: 10 amino acids
( B ) TYPE: amino acid
( C ) TOPOLOGY: circular ( i i ) SEQUENCE DESCRIPTION: SEQ ID NO:31:

Lys Thr Lys Cys Lys Phe Leu Lys Lys Cys
1               5                   1 0

( 2 ) INFORMATION FOR SEQ ID NO:32:

( i ) SEQUENCE CHARACTERISTICS:
( A ) LENGTH: 6 amino acids
( B ) TYPE: amino acid
( C ) TOPOLOGY: circular ( i i ) SEQUENCE DESCRIPTION: SEQ ID NO:32:

Lys Phe Leu Lys Lys Thr
1               5

( 2 ) INFORMATION FOR SEQ ID NO:33:

( i ) SEQUENCE CHARACTERISTICS:
( A ) LENGTH: 10 amino acids
( B ) TYPE: amino acid
( C ) TOPOLOGY: circular ( i i ) SEQUENCE DESCRIPTION: SEQ ID NO:33:

Cys Lys Lys Leu Phe Lys Cys Lys Thr Lys
1               5                   1 0

( 2 ) INFORMATION FOR SEQ ID NO:34:

( i ) SEQUENCE CHARACTERISTICS:
( A ) LENGTH: 9 amino acids
( B ) TYPE: amino acid
( C ) TOPOLOGY: circular ( i i ) SEQUENCE DESCRIPTION: SEQ ID NO:34:

```
        Cys  Lys  Lys  Leu  Phe  Lys  Cys  Lys  Thr
        1                  5
```

(2) INFORMATION FOR SEQ ID NO:35:

(i) SEQUENCE CHARACTERISTICS:
        (A) LENGTH: 11 amino acids
        (B) TYPE: amino acid
        (C) TOPOLOGY: circular (i i) SEQUENCE DESCRIPTION: SEQ ID NO:35:

```
        Ile  Lys  Thr  Lys  Cys  Lys  Phe  Leu  Lys  Lys  Cys
        1                  5                            10
```

(2) INFORMATION FOR SEQ ID NO:36:

(i) SEQUENCE CHARACTERISTICS:
        (A) LENGTH: 10 amino acids
        (B) TYPE: amino acid
        (C) TOPOLOGY: circular (i i) SEQUENCE DESCRIPTION: SEQ ID NO:36:

```
        Ile  Lys  Thr  Lys  Lys  Phe  Leu  Lys  Lys  Thr
        1                  5                       10
```

(2) INFORMATION FOR SEQ ID NO:37:

(i) SEQUENCE CHARACTERISTICS:
        (A) LENGTH: 11 amino acids
        (B) TYPE: amino acid
        (C) TOPOLOGY: circular (i i) SEQUENCE DESCRIPTION: SEQ ID NO:37:

```
        Ile  Lys  Phe  Leu  Lys  Phe  Leu  Lys  Phe  Leu  Lys
        1                  5                            10
```

(2) INFORMATION FOR SEQ ID NO:38:

(i) SEQUENCE CHARACTERISTICS:
        (A) LENGTH: 7 amino acids
        (B) TYPE: amino acid
        (C) TOPOLOGY: circular (i i) SEQUENCE DESCRIPTION: SEQ ID NO:38:

```
        Lys  Phe  Leu  Lys  Phe  Leu  Lys
        1                  5
```

(2) INFORMATION FOR SEQ ID NO:39:

(i) SEQUENCE CHARACTERISTICS:
        (A) LENGTH: 9 amino acids
        (B) TYPE: amino acid
        (C) TOPOLOGY: circular (i i) SEQUENCE DESCRIPTION: SEQ ID NO:39:

```
        Arg  Tyr  Val  Arg  Tyr  Val  Arg  Tyr  Val
        1                  5
```

(2) INFORMATION FOR SEQ ID NO:40:

(i) SEQUENCE CHARACTERISTICS:
        (A) LENGTH: 9 amino acids
        (B) TYPE: amino acid
        (C) TOPOLOGY: circular (i i) SEQUENCE DESCRIPTION: SEQ ID NO:40:

```
        Lys  Phe  Phe  Lys  Phe  Phe  Lys  Phe  Phe
        1                  5
```

(2) INFORMATION FOR SEQ ID NO:41:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:41:

Ile Lys Phe Leu Lys Phe Leu Lys Phe Leu
        1                  5                          10

(2) INFORMATION FOR SEQ ID NO:42:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:42:

Lys Lys Lys Lys Lys Lys Phe Leu Phe Leu
        1                  5                          10

(2) INFORMATION FOR SEQ ID NO:43:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:43:

Cys Lys Phe Lys Phe Lys Phe Lys Phe Cys
        1                  5                          10

(2) INFORMATION FOR SEQ ID NO:44:

(i) SEQUENCE CHARACTERISTICS:
        (A) LENGTH: 10 amino acids
        (B) TYPE: amino acid
        (C) TOPOLOGY: circular (ii) SEQUENCE DESCRIPTION: SEQ ID NO:44:

Lys Trp Lys Ala Gln Lys Arg Phe Leu Lys
        1                  5                          10

(2) INFORMATION FOR SEQ ID NO:45:

(i) SEQUENCE CHARACTERISTICS:
        (A) LENGTH: 11 amino acids
        (B) TYPE: amino acid
        (C) TOPOLOGY: circular (ii) SEQUENCE DESCRIPTION: SEQ ID NO:45:

Lys Arg Leu Lys Trp Lys Tyr Lys Gly Lys Phe
        1                  5                          10

We claim:

1. A method for the potentiation of the activity of an antibiotic which comprises coadministering an antibiotic and a peptide selected from the group consisting of:

$(Lys)_{10}$ (SEQ ID NO: 1).
$(Lys-Glu)_5$ (SEQ ID NO: 4).
$(Lys-Phe)_5$ (SEQ ID NO: 5).
Lys—Phe—Leu—Lys—Lys—Thr—Leu (SEQ ID NO: 6).
$(Lys-Phe-Leu)_2$—Lys (SEQ ID NO: 7).
$(Lys-Phe-Leu)_3$—Lys (SEQ ID NO: 8).
$(Arg-Tyr-Val)_3$ (SEQ ID NO: 9).
$(Lys-Phe-Phe)_3$—Lys (Seq ID NO: 10).
$(Lys-Leu-Leu)_3$ (SEQ ID NO: 11).
$(Lys)_6(Phe-Lys)_2$ (SEQ ID NO: 12).
Cys—$(Lys)_5$—Cys
s----------s (SEQ ID NO: 13).

Cys—Lys—Phe—Lys—Lys—Cys
s-----------------------s (SEQ ID NO: 14).

-continued

Lys—Phe—Lys—Cys—Lys—Phe—Lys—Phe—Lys—Cys
   s----------------------------s
(SEQ ID NO: 15).
Lys—Leu—Lys—Cys—Lys—Leu—Lys—Leu—Lys—Cys
   s----------------------------s
(SEQ ID NO: 16).
Arg—Thr—Arg—Cys—Arg—Phe—Lys—Arg—Arg—Cys
   s----------------------------s
(SEQ ID NO: 17).
Lys—Cys—(Lys—Phe—Lys)$_2$—Cys—Lys
   s---------------------s (SEQ ID NO: 18).
Cys—(Lys)$_4$—(Phe)$_4$—Cys
s---------------------s (SEQ ID NO: 19).

Cys—(Lys—Phe—Leu)$_3$—Lys—Cys
s------------------------------s (SEQ ID NO: 20).

Val—Lys—Ala—Leu—Arg—Val—Arg—Arg—Leu (SEQ ID NO: 21)
Lys—Ser—Leu—Ser—Leu—Lys—Arg—Leu—Thr—Tyr—Arg
(SEQ ID NO: 22)
Lys—Val—Arg—Lys—Ser—Phe—Phe—Lys—Val (SEQ ID NO: 23)
Phe—Leu—Lys—Pro—Gly—Lys—Val—Lys—Val (SEQ ID NO: 24)
Lys—Asp—Leu—Lys—Arg—Ile—Lys—Ile (SEQ ID NO: 25)
Lys—Trp—Lys—Ala—Gln—Lys—Arg—Phe—Leu (SEQ ID NO: 26)
Lys—Trp—Lys—Ala—Gln—Lys—Arg—Phe—Leu—Lys
(SEQ ID NO: 27)
Lys—Arg—Leu—Lys—Trp—Lys—Tyr—Lys—Gly—Lys—Phe
(SEQ ID NO: 28)
Cys—Gln—Trp—Lys—Ser—Ser—Asp—Ile—Arg—Cys—Gly—Lys
s---------------------------------------s
(SEQ ID NO: 29)
Cys—Lys—Phe—Leu—Lys—Lys—Cys
s---------------------------s (Seq ID NO: 30)

Lys—Thr—Lys—Cys—Lys—Phe—Leu—Lys—Lys—Cys
   s----------------------------s
(SEQ ID NO: 31)
Lys—Phe—Leu—Lys—Lys—Thr (SEQ ID NO: 32)
Cys—Lys—Lys—Leu—Phe—Lys—Cys—Lys—Thr—Lys
   s--------------------------s (SEQ ID NO: 33)
Cys—Lys—Lys—Leu—Phe—Lys—Cys—Lys—Thr
s--------------------------s (SEQ ID NO: 34)
Ile—Lys—Thr—Lys—Cys—Lys—Phe—Leu—Lys—Lys—Cys
       s---------------------------s
(SEQ ID NO: 35)
Ile—Lys—Thr—Lys—Lys—Phe—Leu—Lys—Lys—Thr
(SEQ ID NO: 36)
Ile—Lys—Phe—Leu—Lys—Phe—Leu—Lys—Phe—Leu—Lys
(SEQ ID NO: 37)
Lys—Phe—Leu—Lys—Phe—Leu—Lys (SEQ ID NO: 38)
Arg—Tyr—Val—Arg—Tyr—Val—Arg—Tyr—Val (SEQ ID NO: 39)
Lys—Phe—Phe—Lys—Phe—Phe—Lys—Phe—Cys (SEQ ID NO: 40)
Ile—Lys—Phe—Leu—Lys—Phe—Leu—Lys—Phe—Leu
(SEQ ID NO: 41)
(Lys)$_6$Phe—Leu—Phe—Leu (SEQ ID NO: 42)
Cys—Lys—Phe—Lys—Phe—Lys—Phe—Lys—Phe—Cys
s---------------------------------------s
(SEQ ID NO: 43
Lys—Trp—Lys—Ala—Gln—Lys—Arg—Phe—Leu—Lys
(SEQ ID NO: 44)
and
Lys—Arg—Leu—Lys—Trp—Lys—Tyr—Lys—Gly—Lys—Phe
(SEQ ID NO: 45).

2. A method as defined in claim 1 where the antibiotic is selected from the group consisting of penicillin derivatives; cephalosporins; aminoglycosides; erythromycin; monobactams; rifamycin and derivatives thereof; chloramphenicol; clindamycin; lincomycin; imipenem; vancomycin; tetracyclines; fusidic acid and novobiocin.

3. A method for the potentiation of the activity of an antibiotic as defined in claim 1 wherein the peptide is of the formula:

(Lys)$_{10}$. (SEQ ID NO: 1).

4. A method for the potentiation of the activity of an antibiotic as defined in claim 1 wherein the peptide is of the formula:

(Lys-Glu)$_5$. (SEQ ID NO: 4).

5. A method for the potentiation of the activity of an antibiotic as defined in claim 1 wherein the peptide is of the formula:

(Lys-Phe)$_5$. (SEQ ID NO: 5).

6. A method for the potentiation of the activity of an antibiotic as defined in claim 1 wherein the peptide is of the formula:

Lys-Phe-Leu-Lys-Lys-Thr-Leu. (SEQ ID NO: 6).

7. A method for the potentiation of the activity of an antibiotic as defined in claim 1 wherein in which the peptide is of the formula:

(Lys-Phe-Leu)$_2$-Lys. (SEQ ID NO: 7).

8. A method for the potentiation of the activity of an antibiotic as defined in claim 1 wherein the peptide is of the formula:

(Lys-Phe-Leu)$_3$-Lys. (SEQ ID NO: 8).

9. A method for the potentiation of the activity of an antibiotic as defined in claim 1 wherein the peptide is of the formula:

(Arg-Tyr-Val)$_3$. (SEQ ID NO: 9).

10. A method for the potentiation of the activity of an antibiotic as defined in claim 1 wherein the peptide is of the formula:

(Lys-Phe-Phe)$_3$-Lys. (Seq ID NO: 10).

11. A method for the potentiation of the activity of an antibiotic as defined in claim 1 wherein the peptide is of the formula:

(Lys-Leu-Leu)$_3$. (SEQ ID NO: 11).

12. A method for the potentiation of the activity of an antibiotic as defined in claim 1 wherein the peptide is of the formula:

(Lys)$_6$(Phe-Lys)$_2$. (SEQ ID NO: 12).

13. A method for the potentiation of the activity of an antibiotic as defined in claim 1 wherein the peptide is of the formula:

Cys—(Lys)$_5$—Cys
s----------s   (SEQ ID NO: 13).

14. A method for the potentiation of the activity of an antibiotic as defined in claim 1 wherein the peptide is of the formula:

Cys—Lys—Phe—Lys—Lys—Cys
s------------------------s   (SEQ ID NO: 14).

15. A method for the potentiation of the activity of an antibiotic as defined in claim 1 wherein the peptide is of the formula:

Lys—Phe—Lys—Cys—Lys—Phe—Lys—Phe—Lys—Cys
         s----------------------------s
(SEQ ID NO: 15).

16. A method for the potentiation of the activity of an antibiotic as defined in claim 1 wherein the peptide is of the formula:

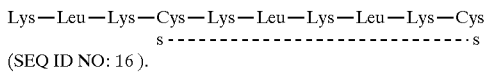
(SEQ ID NO: 16).

17. A method for the potentiation of the activity of an antibiotic as defined in claim 1 wherein the peptide is of the formula:

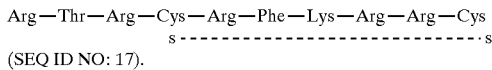
(SEQ ID NO: 17).

18. A method for the potentiation of the activity of an antibiotic as defined in claim 1 wherein the peptide is of the formula:

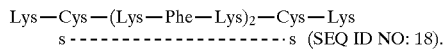

19. A method for the potentiation of the activity of an antibiotic as defined in claim 1 wherein the peptide is of the formula:

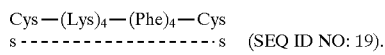

20. A method for the potentiation of the activity of an antibiotic as defined in claim 1 wherein the peptide is of the formula:

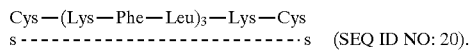

21. A method for the potentiation of the activity of an antibiotic as defined in claim 1 wherein the peptide is of the formula:

Val-Lys-Ala-Leu-Arg-Val-Arg-Arg-Leu. (SEQ ID NO: 21).

22. A method for the potentiation of the activity of an antibiotic as defined in claim 1 wherein the peptide is of the formula:

Lys-Ser-Leu-Ser-Leu-Lys-Arg-Leu-Thr-Tyr-Arg.(SEQ ID NO:22).

23. A method for the potentiation of the activity of an antibiotic as defined in claim 1 wherein the peptide is of the formula:

Lys-Val-Arg-Lys-Ser-Phe-Phe-Lys-Val (SEQ ID NO: 23).

24. A method for the potentiation of the activity of an antibiotic as defined in claim 1 wherein the peptide is of the formula:

Phe-Leu-Lys-Pro-Gly-Lys-Val-Lys-Val.(SEQ ID NO: 24).

25. A method for the potentiation of the activity of an antibiotic as defined in claim 1 wherein the peptide is of the formula:

Lys-Asp-Leu-Lys-Arg-Ile-Lys-Ile.(SEQ ID NO: 25).

26. A method for the potentiation of the activity of an antibiotic as defined in claim 1 wherein the peptide is of the formula:

Lys-Trp-Lys-Ala-Gln-Lys-Arg-Phe-Leu.(SEQ ID NO: 26).

27. A method for the potentiation of the activity of an antibiotic as defined in claim 1 wherein the peptide is of the formula:

Lys-Trp-Lys-Ala-Gln-Lys-Arg-Phe-Leu-Lys.(SEQ ID NO: 27).

28. A method for the potentiation of the activity of an antibiotic as defined in claim 1 wherein the peptide is of the formula:

Lys-Arg-Leu-Lys-Trp-Lys-Tyr-Lys-Gly-Lys-Phe.(SEQ ID NO:28).

29. A method for the potentiation of the activity of an antibiotic as defined in claim 1 wherein the peptide is of the formula:

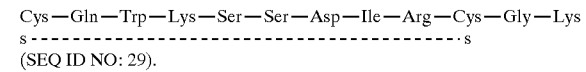
(SEQ ID NO: 29).

30. A method for the potentiation of the activity of an antibiotic as defined in claim 1 wherein the peptide is of the formula:

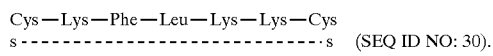

31. A method for the potentiation of the activity of an antibiotic as defined in claim 1 wherein the peptide is of the formula:

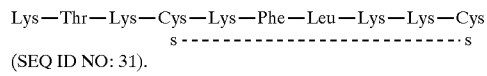
(SEQ ID NO: 31).

32. A method for the potentiation of the activity of an antibiotic as defined in claim 1 wherein the peptide is of the formula:

Lys-Phe-Leu-Lys-Lys-Thr.(SEQ ID NO: 32).

33. A method for the potentiation of the activity of an antibiotic as defined in claim 1 wherein the peptide is of the formula:

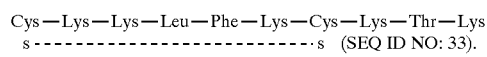

34. A method for the potentiation of the activity of an antibiotic as defined in claim 1 wherein the peptide is of the formula:

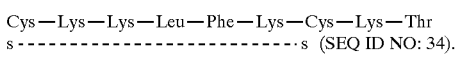

35. A method for the potentiation of the activity of an antibiotic as defined in claim 1 wherein the peptide is of the formula:

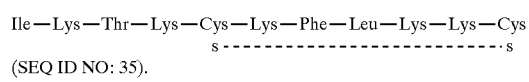
(SEQ ID NO: 35).

36. A method for the potentiation of the activity of an antibiotic as defined in claim 1 wherein the peptide is of the formula:

Ile-Lys-Thr-Lys-Lys-Phe-Leu-Lys-Lys-Thr.(SEQ ID NO: 36).

37. A method for the potentiation of the activity of an antibiotic as defined in claim 1 wherein the peptide is of the formula:

Ile-Lys-Phe-Leu-Lys-Phe-Leu-Lys-Phe-Leu-Lys.(SEQ ID NO: 37).

38. A method for the potentiation of the activity of an antibiotic as defined in claim 1 wherein the peptide is of the formula:

Lys-Phe-Leu-Lys-Phe-Leu-Lys.(SEQ ID NO: 38).

39. A method for the potentiation of the activity of an antibiotic as defined in claim 1 wherein the peptide is of the formula:

Arg-Tyr-Val-Arg-Tyr-Val-Arg-Tyr-Val.(SEQ ID NO: 39).

40. A method for the potentiation of the activity of an antibiotic as defined in claim 1 wherein the peptide is of the formula:

Lys-Phe-Phe-Lys-Phe-Phe-Lys-Phe-Cys.(SEQ ID NO: 40).

41. A method for the potentiation of the activity of an antibiotic as defined in claim 1 wherein the peptide is of the formula:

Ile-Lys-Phe-Leu-Lys-Phe-Leu-Lys-Phe-Leu.(SEQ ID NO:41).

42. A method for the potentiation of the activity of an antibiotic as defined in claim 1 wherein the peptide is of the formula:

$(Lys)_6$Phe-Leu-Phe-Leu.(SEQ ID NO:42).

43. A method for the potentiation of the activity of an antibiotic as defined in claim 1 wherein the peptide is of the formula:

Cys—Lys—Phe—Lys—Phe—Lys—Phe—Lys—Phe—Cys
s--------------------------------------------s
(SEQ ID NO: 43.

44. A method for the potentiation of the activity of an antibiotic as defined in claim 1 wherein the peptide is of the formula:

Lys-Trp-Lys-Ala-Gln-Lys-Arg-Phe-Leu-Lys.(SEQ ID NO: 44).

45. A method for the potentiation of the activity of an antibiotic as defined in claim 1 wherein the peptide is of the formula:

Lys-Arg-Leu-Lys-Trp-Lys-Tyr-Lys-Gly-Lys-Phe.(SEQ ID NO: 45).

* * * * *